United States Patent
Albenge et al.

(10) Patent No.: US 11,820,905 B2
(45) Date of Patent: Nov. 21, 2023

(54) PROCESS OF PREPARATION OF AN AQUEOUS GEL INK WITH FIXED COLOR COMPRISING GOLD NANOPARTICLES

(71) Applicants: SOCIETE BIC, Clichy (FR); UNIVERSITE DE HAUTE ALSACE, Mulhouse (FR); CENTRE NATIONAL DE LA RECHERCHE SCIENTIFIQUE, Paris (FR)

(72) Inventors: Olivier Albenge, Clichy (FR); Romain Metillon, Clichy (FR); Karine Mougin, Paris (FR); Feriel Ghellal, Clichy (FR); Arnaud Spangenberg, Mulhouse (FR)

(73) Assignees: SOCIETE BIC, Clichy (FR); UNIVERSITE DE HAUTE ALSACE, Mulhouse (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 155 days.

(21) Appl. No.: 17/631,099

(22) PCT Filed: Aug. 28, 2020

(86) PCT No.: PCT/EP2020/074113
§ 371 (c)(1),
(2) Date: Jan. 28, 2022

(87) PCT Pub. No.: WO2021/038061
PCT Pub. Date: Mar. 4, 2021

(65) Prior Publication Data
US 2022/0275227 A1 Sep. 1, 2022

(30) Foreign Application Priority Data
Aug. 29, 2019 (EP) ..................... 19306051

(51) Int. Cl.
*C09D 11/17* (2014.01)
*C07C 69/618* (2006.01)
*B43K 1/12* (2006.01)
*B82Y 30/00* (2011.01)

(52) U.S. Cl.
CPC ............... *C09D 11/17* (2013.01); *B43K 1/12* (2013.01); *B82Y 30/00* (2013.01); *C07C 69/618* (2013.01)

(58) Field of Classification Search
CPC ....... C09D 11/17; C09D 11/16; C07C 69/618; B43K 1/12; B43K 1/006; B82Y 30/00
USPC .................. 401/198; 523/215; 524/492, 493
See application file for complete search history.

(56) References Cited

U.S. PATENT DOCUMENTS

| | | | |
|---|---|---|---|
| 8,870,998 B2 | 10/2014 | Nolte et al. | |
| 9,975,110 B1 | 5/2018 | Chou et al. | |
| 2005/0204956 A1 | 9/2005 | Berkei et al. | |
| 2006/0194057 A1 | 8/2006 | Pfluecker et al. | |
| 2010/0247783 A1 | 9/2010 | Breton et al. | |
| 2013/0001479 A1* | 1/2013 | Kanehara ............... | C09D 11/52 977/773 |
| 2016/0257860 A1 | 9/2016 | Rink | |
| 2022/0243083 A1* | 8/2022 | Enriquez .............. | B01J 13/0034 |

FOREIGN PATENT DOCUMENTS

| | | |
|---|---|---|
| CN | 1800272 A | 7/2006 |
| CN | 101027151 A | 8/2007 |
| CN | 101683693 A | 3/2010 |
| CN | 106867315 A | 6/2017 |
| CN | 110167885 A | 8/2019 |
| JP | 2946747 B2 | 9/1999 |
| JP | 2008125435 A | 6/2008 |
| WO | 2006072959 A1 | 7/2006 |

OTHER PUBLICATIONS

International Search Report and Written Opinion in International Application No. PCT/EP2020/074113, dated Nov. 6, 2020 (7 pages).

* cited by examiner

*Primary Examiner* — David J Walczak
(74) *Attorney, Agent, or Firm* — Bookoff McAndrews, PLLC

(57) ABSTRACT

A process for preparing in situ an aqueous gel ink with fixed color comprising the following steps: (i) preparing a gel-based matrix of aqueous ink comprising ester(s) of retinol represented by formula (I), and (ii) adding a solution of gold salts (Au3+) to the gel-based matrix of aqueous ink prepared in step (i), to obtain an aqueous gel ink with fixed color with gold nanoparticles dispersed therein. An aqueous gel ink with fixed color obtained according to the process of the invention, comprising the ester of retinol represented by formula (I) and gold nanoparticles. A writing instrument comprising an aqueous gel ink with fixed color.

(I)

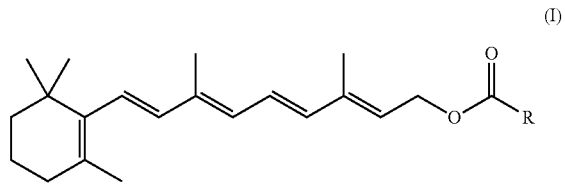

20 Claims, No Drawings

PROCESS OF PREPARATION OF AN AQUEOUS GEL INK WITH FIXED COLOR COMPRISING GOLD NANOPARTICLES

CROSS-REFERENCE TO RELATED APPLICATIONS

This application is the U.S. national phase entry under 35 U.S.C. § 371 of International Application No. PCT/EP2020/074113, filed Aug. 28, 2020, which claims priority to European Patent Application No. 19306051.4, filed Aug. 29, 2019, the entire contents of which are incorporated herein by reference.

The present invention concerns a process for preparing in situ an aqueous gel ink with fixed color, and to aqueous gel inks with fixed color comprising said ester(s) of retinol (I) represented by formula (I) and gold nanoparticles, obtained according to the process of the invention, and free from any dye and pigment. The invention also concerns a writing instrument comprising an aqueous gel ink with fixed color according to the invention.

One of the main objectives of the present invention is to replace all type of dyes and pigments normally present in aqueous gel inks, which have the disadvantage of being expensive and causing high production costs.

Another objective of the present invention is to replace all types of dyes and pigments normally present in aqueous gel inks, which have the disadvantage of being irritating to biological membranes, for example skin and eyes, and may cause allergies.

The inventors have surprisingly found that the new aqueous gel inks containing nanoparticles-based are also resistant to UV light thereby improving light stability over time. To this end, the inventors have developed a specific process through which it is possible to obtain new aqueous gel inks with fixed color when writing by replacing former aqueous gel inks containing dyes and pigments by new ones that are nanoparticles-based. The process developed within the framework of the invention also presents the advantage of being performed in aqueous media, and therefore to be a "green process". In addition, the process of the invention is performed at low temperature ranges, works in an ecologically viable manner, and also takes account of ecological requirements.

The present invention relates to a process for preparing in situ an aqueous gel ink with fixed color comprising the following steps:
(i) preparing a gel-based matrix of aqueous ink comprising ester(s) of retinol represented by the following formula (I):

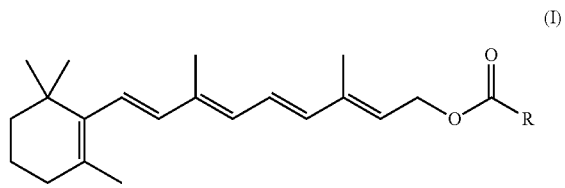

(I)

Wherein R represents a $C_1$-$C_6$ aliphatic group, said aliphatic group being optionally substituted with at least one hydroxy, halogen, amino, $C_1$-$C_3$ alkyl and/or $C_1$-$C_3$ alkoxy group, said aliphatic group being preferably a $C_1$-$C_6$ alkyl group, preferably a $C_1$-$C_4$ alkyl group, preferably unsubstituted, preferably a methyl group, and (ii) adding a solution of gold salts ($Au^{3+}$) to the gel-based matrix of aqueous ink prepared in step (i), to obtain an aqueous gel ink with fixed color with gold nanoparticles dispersed therein.

In the sense of the invention, the term "in situ" means that the gold nanoparticles present in the aqueous gel ink of the invention are synthetized directly in the gel-based matrix of the aqueous ink.

In the sense of the invention, the term "fixed color" is intended to mean that the color of the aqueous gel ink by visual observation is the same before application on absorbing support, and after application on absorbing support, specifically paper, cardboard or textiles, within 7 calendar days (one week).

For the purposes of the present invention, the term "ink" is intended to mean a "writing ink" which is intended to be used in a writing instrument, and in particular in a pen. A writing ink should not be confused with a "printing ink" which is used in printing machines and which does not have the same technical constraints and thus the same specifications. Indeed, a writing ink must not contain solid particles of which the size is greater than the channels of the writing instrument, in order to avoid blocking them, which would inevitably lead to writing being irreversibly stopped. In addition, it must allow an ink flow rate suitable for the writing instrument used, in particular a flow rate of between 100 and 500 mg/200 m of writing, and advantageously between 150 and 400 mg/200 m of writing. It must also dry sufficiently rapidly to avoid smudging the writing medium. It must also avoid the problems of migration (bleeding) over time. Thus, the ink according to the present invention will be suitable for the writing instrument for which it is intended, in particular for a pen.

In addition, a "writing ink" must not be too fluid, so as to avoid leaks during writing. However, it must be sufficiently fluid to facilitate the flow of the writing action.

In the particular case of the invention, the writing ink can be more specifically a "gel ink" (which corresponds therefore to a thixotropic ink), in particular the viscosity measured at rest (at a shear rate of 0.01 $s^{-1}$) at 20° C. is different and in particular higher than the viscosity measured with a shear rate of 100 $s^{-1}$ at 20° C. using the same rheometer such as a cone-and-plate rheometer for example Malvern KINEXUS with a cone of 60 mm and an angle of 1°. In a particular embodiment, the viscosity of the gel ink according to the present invention measured under these conditions ranges from 1,000 to 7,000 mPa·s, advantageously from 2,000 to 5,000 mPa·s, and more advantageously from 2,500 to 3,500 mPa·s, with a shear rate of 1 $s^{-1}$, and advantageously from 5 to 50 mPa·s, more advantageously from 7 to 40 mPa·s, and still more advantageously from 10 to 20 mPa·s with a shear rate of 5,000 $s^{-1}$. Advantageously, such a viscosity is stable during storage for at least three months at 40° C. and 20% relative humidity, in particular the viscosity will not have a more than 50% decrease. More advantageously, the return to viscosity at rest after shear is very quick, advantageously at most a few minutes, in order to avoid the static leakage in the minutes after writing.

In the present invention, the gel-based matrix of aqueous ink prepared in step (i) may comprise from 50 to 95%, preferably from 60 to 90%, and more preferably from 70 to 85%, by weight of water.

The gel-based matrix of aqueous ink prepared in step (i) may also comprise classic gel ink ingredients such as solvents, antimicrobial agents, corrosion inhibitors, antifoam agents, rheology modifiers, etc. The gel ink ingredients used to prepare the gel-based matrix of aqueous ink of step (i) will be largely described below, in relation with the subject-matter of the aqueous gel ink with fixed color of the invention.

According to a preferred embodiment of the invention, the process for preparing in situ an aqueous gel ink with fixed color comprising the following steps:
(i) preparing a gel-based matrix of aqueous ink comprising ester(s) of retinol represented by the following formula (I):

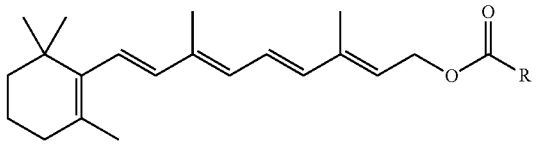

Wherein R represents a $C_1$-$C_6$ aliphatic group, said aliphatic group being optionally substituted with at least one hydroxy, halogen, amino, $C_1$-$C_3$ alkyl and/or $C_1$-$C_3$ alkoxy group, said aliphatic group being preferably a $C_1$-$C_6$ alkyl group, preferably a $C_1$-$C_4$ alkyl group, preferably unsubstituted, preferably a methyl group, and (ii) adding a solution of gold salts ($Au^{3+}$) to the gel-based matrix of aqueous ink prepared in step (i), to obtain an aqueous gel ink with fixed color with gold nanoparticles dispersed therein.

In the most preferred embodiment of the invention, the process for preparing in situ an aqueous gel ink with fixed color comprising the following steps:
(i) preparing a gel-based matrix of aqueous ink comprising ester(s) of retinol represented by the following formula (I):

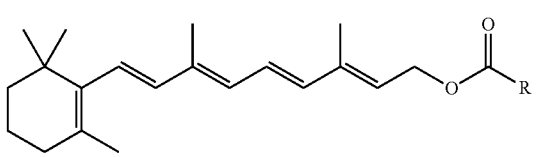

wherein R represents a methyl group, and
(ii) adding a solution of gold salts ($Au^{3+}$) to the gel-based matrix of aqueous ink prepared in step (i), to obtain an aqueous gel ink with fixed color with gold nanoparticles dispersed therein The ester of retinol represented by the formula (I), wherein R represents a methyl group, is commonly known retinyl acetate.

The retinyl acetate (CAS number: 127-47-9), also known as vitamin A acetate, may be purchased via Sigma-Aldrich. The retinyl acetate may be added in the form of a solution or in the form of powder.

The ester (s) of retinol represented by the following formula (I) wherein R represents a $C_1$-$C_6$ aliphatic group, said aliphatic group being optionally substituted with at least one hydroxy, halogen, amino, $C_1$-$C_3$ alkyl and/or $C_1$-$C_3$ alkoxy group, said aliphatic group being preferably a $C_1$-$C_6$ alkyl group, preferably a $C_1$-$C_4$ alkyl group, preferably unsubstituted, preferably a methyl group reduces the gold salts to elemental metal (i.e. oxidation state: 0).

In a preferred embodiment, the concentration of the ester (s) of retinol represented by formula (I) wherein R represents a $C_1$-$C_6$ aliphatic group, said aliphatic group being optionally substituted with at least one hydroxy, halogen, amino, $C_1$-$C_3$ alkyl and/or $C_1$-$C_3$ alkoxy group, said aliphatic group being preferably a $C_1$-$C_6$ alkyl group, preferably a $C_1$-$C_4$ alkyl group, preferably unsubstituted, preferably a methyl group in the gel-based matrix of aqueous ink of step (i) ranges from 0.10 to 0.50 mol·$L^{-1}$, preferably from 0.20 to 0.40 mol·$L^{-1}$, and more preferably from 0.25 to 0.35 mol·$L^{-1}$.

In the present invention, the solution of gold salts ($Au^{3+}$) is advantageously a solution of gold (III) chloride trihydrate $HAuCl_4 \cdot 3H_2O$. Gold nanoparticles are formed when contacting the solution of gold salts with the ester (s) of retinol represented by formula (I) wherein R represents a $C_1$-$C_6$ aliphatic group, said aliphatic group being optionally substituted with at least one hydroxy, halogen, amino, $C_1$-$C_3$ alkyl and/or $C_1$-$C_3$ alkoxy group, said aliphatic group being preferably a $C_1$-$C_6$ alkyl group, preferably a $C_1$-$C_4$ alkyl group, preferably unsubstituted, preferably a methyl group In a preferred embodiment, the concentration of gold salts ($Au^{3+}$) in the gel-based matrix of aqueous ink of step (ii) ranges from 0.004 to 0.05 mol·$L^{-1}$, and preferably 0.005 to 0.04 mol·$L^{-1}$.

The addition of a solution of gold salts ($Au^{3+}$) to the gel-based matrix of aqueous ink prepared in step (i) can be made by continuous injection.

In a preferred embodiment, the gold nanoparticles have the shape of spheres or polyhedral shape, preferably polyhedral shape, and more preferably triangular, square, rectangular shapes.

In a preferred embodiment, the molar ratio between the gold salts ($Au^{3+}$) and ester (s) of retinol represented by formula (I) wherein R represents a $C_1$-$C_6$ aliphatic group, said aliphatic group being optionally substituted with at least one hydroxy, halogen, amino, $C_1$-$C_3$ alkyl and/or $C_1$-$C_3$ alkoxy group, said aliphatic group being preferably a C1-C6 alkyl group, preferably a $C_1$-$C_4$ alkyl group, preferably unsubstituted, preferably a methyl group ranges from 0.005:1 to 0.50:1, and preferably from 0.005:1 to 0.25:1.

The present invention also concerns an aqueous gel ink with fixed color obtained according to the process of the invention, said aqueous gel comprising ester(s) of retinol represented by formula (I) wherein R represents a $C_1$-$C_6$ aliphatic group, said aliphatic group being optionally substituted with at least one hydroxy, halogen, amino, $C_1$-$C_3$ alkyl and/or $C_1$-$C_3$ alkoxy group, said aliphatic group being preferably a $C_1$-$C_6$ alkyl group, preferably a $C_1$-$C_4$ alkyl group, preferably unsubstituted, preferably a methyl group and gold nanoparticles.

The process according to the invention enables to obtain an aqueous ink composition which exhibits a plasmon effect (plasmon color).

In a preferred embodiment, the present invention concerns an aqueous gel ink with fixed color obtained according to the process of the invention, said aqueous gel comprising retinyl acetate and gold nanoparticles.

The ester (s) of retinol represented by formula (I) wherein R represents a $C_1$-$C_6$ aliphatic group, said aliphatic group being optionally substituted with at least one hydroxy, halogen, amino, $C_1$-$C_3$ alkyl and/or $C_1$-$C_3$ alkoxy group, said aliphatic group being preferably a $C_1$-$C_6$ alkyl group, preferably a $C_1$-$C_4$ alkyl group, preferably unsubstituted, preferably a methyl group and gold nanoparticles of the aqueous gel ink of the invention are as defined above in relation with the subject-matter of the process of the invention.

Depending on their size, shape, and distance, the color of the dispersion of the gold nanoparticles can change, as well as its properties. This is due to the plasmon resonance. The exposure of the gold nanoparticles to a certain frequency of waves brings the electrons to gather in a certain place, which changes in accordance with the size and shape of the gold nanoparticles. This agglomeration of electrons provokes an anisotropy of the gold nanoparticles, which will then lead to a change of light absorption and scattering, resulting in a specific color. Plasmon resonance is also affected by the distance between the gold nanoparticles due to the coupling of said gold nanoparticles. Indeed, the closer the gold nanoparticles are, the more they will interact with each other, which will increase their coupling effect also called plasmon effect. In the same way, the shape influences the plasmon resonance.

In the aqueous gel ink with fixed color of the invention, the amount of ester(s) of retinol represented by formula (I) wherein R represents a $C_1$-$C_6$ aliphatic group, said aliphatic group being optionally substituted with at least one hydroxy, halogen, amino, $C_1$-$C_3$ alkyl and/or $C_1$-$C_3$ alkoxy group, said aliphatic group being preferably a $C_1$-$C_6$ alkyl group, preferably a $C_1$-$C_4$ alkyl group, preferably unsubstituted, preferably a methyl group, advantageously ranges from 3 to 5.5%, and more advantageously from 3.5 to 5%, by weight relative to the total weight of the aqueous gel ink.

In the aqueous gel ink with fixed color of the invention, the gold nanoparticles have preferably the shape of spheres.

In the aqueous gel ink with fixed color of the invention, the gold nanoparticles of the invention have preferably an average particle size ranging from 10 to 250 nm, and more preferably from 50 to 200 nm. This average particle size is determined by analysis of 2D images (microscope: JEOL ARM 200), according to the standard ISO9001:2015.

In the aqueous gel ink with fixed color of the invention, the amount of gold nanoparticles advantageously ranges from 0.05 to 3%, and more advantageously from 0.10 to 2%, by weight relative to the total weight of the aqueous gel ink.

In the aqueous gel ink with fixed color of the invention, the amount of water advantageously ranges from 50 to 95%, more advantageously from 60 to 90%, and even more advantageously from 70 to 85%, by weight relative to the total weight of the aqueous gel ink.

The aqueous gel ink with fixed color of the invention may also comprise classic gel ink ingredients such as solvents, antimicrobial agents, corrosion inhibitors, antifoam agents, rheology modifiers, as described below. These gel ink ingredients are added to the gel-based matrix of aqueous ink in step (i) of the process of the invention.

The aqueous gel ink of the invention may comprise a solvent. Among the solvents that can be used, mention may be made of polar solvents miscible in water such as:
  glycol ethers such as triethylene glycol, polyethylene glycol, diethylene glycol monoethyl ether, diethylene-glycol-mono butyl ether, dipropyleneglycol monobutyl ether, tripropylene glycol monomethyl ether, phenoxyethanol, phenoxypropanol,
  alcohols: linear or branched alcohol in $C_1$-$C_{15}$ such as isopropanol, butanol, isobutanol, pentanol, benzyl alcohol, glycerin, diglycerin, polyglycerin,
  esters such as ethyl acetate or propyl acetate,
  carbonate esters such as propylene carbonate or ethylene carbonate,
  ketones such as methylisobutylketone (MIBK), acetone or cyclohexanone, and
  mixtures thereof.

In a preferred embodiment, the solvent is chosen in the group consisting of glycol ethers, and more preferably is chosen in the group consisting of triethylene glycol, polyethylene glycol, diethylene glycol monoethyl ether, diethylene-glycol-mono butyl ether, dipropyleneglycol monobutyl ether, tripropylene glycol monomethyl ether, phenoxyethanol, phenoxypropanol, and mixtures thereof. In a further advantageous embodiment the solvent is chosen in the group consisting of triethylene glycol, polyethylene glycol, and mixture thereof.

Advantageously, the solvent is present in the aqueous gel ink of the invention in an amount ranging from 5 to 35%, more advantageously from 9 to 30%, and even more advantageously from 11 to 25%, by weight relative to the total weight of the aqueous gel ink.

The aqueous gel ink of the invention may comprise an antimicrobial agent such as isothiazolinone (ACTICIDE® from Thor), preferably chosen in the group consisting of 1,2-benzisothiazolin-3-one, 2-methyl-4-isothiazolin-3-one, and mixture thereof.

Advantageously, the antimicrobial agent is present in the aqueous gel ink of the invention in an amount ranging from 0.01 to 0.5%, and more advantageously from 0.1 to 0.2%, by weight relative to the total weight of the aqueous gel ink.

The aqueous gel ink of the invention may comprise a corrosion inhibitor, preferably chosen in the group consisting of tolytriazole, benzotriazole, and mixture thereof.

Advantageously, the corrosion inhibitor is present in the aqueous gel ink of the invention in an amount ranging from 0.05 to 1%, more advantageously from 0.07 to 0.5%, and even more preferably from 0.08 to 0.15%, by weight relative to the total weight of the aqueous gel ink.

The aqueous gel ink of the invention may comprise an antifoam agent, preferably a polysiloxane-based antifoam agent, and more preferably an aqueous emulsion of modified polysiloxane (such as MOUSSEX® from Synthron, TEGO® Foamex from Evonik).

Advantageously, the antifoam agent is present in the aqueous gel ink of the invention in an amount ranging from 0.05 to 1%, more advantageously from 0.1 to 0.5%, and even more advantageously from 0.2 to 0.4%, by weight relative to the total weight of the aqueous gel ink.

The aqueous gel ink of the invention may comprise a rheology modifier capable of generating a gelling effect, preferably chosen in the group consisting of xanthan gum, gum arabic, and mixture thereof.

Advantageously, the rheology modifier is present in an amount ranging from 0.08 to 2%, more preferably from 0.2 to 0.8%, and even more preferably from 0.3 to 0.6%, by weight relative to the total weight of the aqueous gel ink.

The aqueous gel ink with fixed color of the invention may also comprise other additives such as:
  pH regulators like sodium hydroxide and triethanolamine,
  lubricants,
  coalescing agents,
  crosslinking agents,
  wetting agents,
  plasticizers,
  antioxidants, and
  UV stabilizers.

When present, these additives are added to the gel-based matrix of aqueous ink in step (i) of the process of the invention.

In one aspect, the invention relates to a process for preparing in situ an aqueous ink with fixed color comprising the following steps:
(i) preparing a matrix of aqueous ink, comprising ester(s) of retinol represented by the following formula (I):

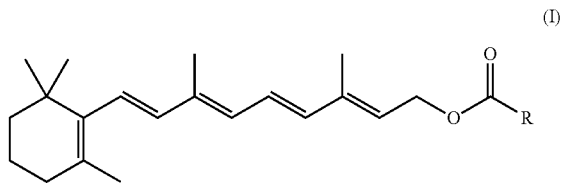

(I)

Wherein R represents a $C_1$-$C_6$ aliphatic group, said aliphatic group being optionally substituted with at least one hydroxy, halogen, amino, $C_1$-$C_3$ alkyl and/or $C_1$-$C_3$ alkoxy group, said aliphatic group being preferably a $C_1$-$C_6$ alkyl group, preferably a $C_1$-$C_4$ alkyl group, preferably unsubstituted, preferably a methyl group, and
(ii) adding a solution of gold salts ($Au^{3+}$) to the matrix of aqueous ink, prepared in step (i), to obtain an aqueous ink with fixed color with gold nanoparticles dispersed therein.

In one aspect, the invention relates to an aqueous ink with fixed color obtained according to the above mentioned process of the invention, in particular said aqueous ink comprising ester(s) of retinol represented by formula (I) and gold nanoparticles, in particular which are as defined in the present disclosure.

The aqueous ink with fixed color of the invention may also comprise classic ink ingredients as described previously such as solvents, antimicrobial agents, corrosion inhibitors, antifoam agents, rheology modifiers. These ingredients are added to the matrix of aqueous ink in step (i) of the process of the invention.

In one aspect, the invention relates to the use of the aqueous ink, more specifically of the aqueous gel ink, of fixed color as defined above for writing onto an absorbing support. In one embodiment, the absorbing support is a porous substrate, specifically paper, cardboard, or textiles.

The present invention also concerns a method of writing with an aqueous ink, more specifically an aqueous gel ink, of fixed color comprising the step of writing onto an absorbing support, wherein the absorbing support is a porous substrate, specifically paper, cardboard or textiles, with an aqueous ink with fixed color according to the invention.

After writing onto an absorbing support with the aqueous ink, specifically the aqueous gel ink, of fixed color of the invention, the distance between the gold nanoparticles within the aqueous gel ink applied on absorbing support is lower than 2 μm, preferably varies from 50 nm to 2 μm, and more preferably varies from 200 nm to 1 μm.

Finally, the present invention concerns a writing instrument comprising:
an axial barrel containing the aqueous ink, more specifically the aqueous gel ink, according to the invention, and
a pen body which delivers the aqueous ink stored in the axial barrel.

The writing instrument of the invention may be chosen in the group consisting of gel pens, felt pens, correction fluid, markers, and preferably gel pens.

In addition to the foregoing, the invention also comprises other provisions which will emerge from the additional description which follows, which relates to the preparation of aqueous gel inks with fixed color according to the process of the invention and comparative examples.

EXAMPLES

Example 1

Preparation of an Aqueous Gel Ink with Fixed Color Based on Retinyl Acetate and Gold Nanoparticles, According to the Process of the Present Invention In a first step (i), a gel-based matrix of aqueous ink was prepared by mixing 15 g of triethylene glycol (solvent), 4 g of polyethylene glycol (solvent), 0.19 g of Acticide® MBS (antimicrobial agent), and 0.10 g of Additie RC8221 (corrosion inhibitor). The mixture was homogeneized with a homogeneizer mixer at a speed of 15 m·s$^{-1}$ during 15 minutes and heated at a temperature of 35° C. Then, 0.40 g of xanthan gum (rheology modifier) was added to the mixture. The mixture was homogenized with a homogenizing mixer at a speed of 15 m·s$^{-1}$ during 15 minutes at a temperature of 35° C. 80.01 g of deionized water was slowly added to the mixture. The mixture was left to stand for 2 h30. Then, 0.30 g of Moussee S 9092 (antifoam agent) was added. The mixture was homogenized with a homogenizing mixer at a speed of 15 m·s$^{-1}$ during 30 minutes at a temperature of 35° C. The gel-based matrix of aqueous ink obtained was cooled at room temperature (25° C.). Then, 1 mL of the obtained gel-based matrix of aqueous ink was mixed with 0.05 g of retinyl acetate (Sigma-Aldrich). The mixture was homogeneized with a homogeneizer mixer at a speed of 400 rpm during 15 minutes.

In a second step (ii), 100 μL of a solution of gold (III) chloride trihydrate (520918-1G from Sigma-Aldrich) (200 mM) was introduced into the mixture at a speed of 400 rpm during 15 minutes.

After the addition of the solution of gold (III) chloride trihydrate by continuous injection, the color of the aqueous gel ink was dark blue.

The average particle size of the gold nanoparticles present within the aqueous gel ink is of 50 nm by analysis of 2D images (microscope: JEOL ARM 200), according to the standard ISO9001:2015.

When the obtained aqueous gel ink with fixed color was written on cellulosic paper, the color appeared immediately dark blue and did not change after all.

Thus, the color of the ink is the same before application on cellulosic paper and after application on cellulosic paper. Furthermore, a visual assessment of the color of this aqueous gel ink was realized over time.

As can be seen from Table 1, the color of the aqueous gel ink did not change over time.

TABLE 1

Example 1 - Visual assessment of the color of aqueous gel ink over time

| Time | 0 min | 2 min | 1 hour | 1 day | 1 week (7 calendar days) |
|---|---|---|---|---|---|
| Color of the aqueous gel ink before application on cellulosic paper | Dark blue | Dark blue | Dark blue | Dark blue | Dark blue |
| Color of the aqueous gel ink after application on cellulosic paper | Dark blue | Dark Blue | Dark blue | Dark blue | Dark blue |

Comparative Example 1

Preparation of an Aqueous Gel Ink Based on Retinyl Palmitate and Gold Nanoparticles In a first step, a gel-based matrix of aqueous ink was prepared by mixing 15 g of triethylene glycol (solvent), 4 g of polyethylene glycol (solvent), 0.19 g of Acticide® MBS (antimicrobial agent), and 0.10 g of Additie RC8221 (corrosion inhibitor). The mixture was homogeneized with a homogeneizer mixer at a speed of 15 m·s$^{-1}$ during 15 minutes and heated at a temperature of 35° C. Then, 0.40 g of xanthan gum (rheology modifier) was added to the mixture. The mixture was homogenized with a homogenizing mixer at a speed of 15 m·s$^{-1}$ during 15 minutes at a temperature of 35° C. 80.01 g of deionized water was slowly added to the mixture. The mixture was left to stand for 2 h30. Then, 0.30 g of Moussee S 9092 (antifoam agent) was added. The mixture was homogenized with a homogenizing mixer at a speed of 15 m·s$^{-1}$ during 30 minutes at a temperature of 35° C. The gel-based matrix of aqueous ink obtained was cooled at room temperature (25° C.). Then, 1 mL of the obtained gel-based matrix of aqueous ink was mixed with 0.05 g of retinyl palmitate (CAS number: 79-81-2, from Sigma-Aldrich). The mixture was homogeneized with a homogeneizer mixer at a speed of 400 rpm during 15 minutes.

In a second step, 100 μL of a solution of gold (III) chloride trihydrate (520918-1G from Sigma-Aldrich) (200 mM) was introduced into the mixture at a speed of 400 rpm during 15 minutes. After the addition of the solution of gold (III) chloride trihydrate by continuous injection, the color of the aqueous gel ink was translucent yellow.

When the obtained aqueous gel ink was written on cellulosic paper, the color did not change and remained translucent yellow.

Furthermore, a visual assessment of the color of this aqueous gel ink on cellulosic paper was realized over time.

As can be seen from Table 2, the color of the aqueous gel ink on cellulosic paper appears brown after 1 week.

Thus, the color of the ink is not the same before application on cellulosic paper and after application on cellulosic paper over time.

Comparative Example 2

Preparation of an Aqueous Gel Ink with Variable Color Based on Retinyl Acetate and Silver Nanoparticles In a first step (i), a gel-based matrix of aqueous ink was prepared by mixing 15 g of triethylene glycol (solvent), 4 g of polyethylene glycol (solvent), 0.19 g of Acticide® MBS (antimicrobial agent), and 0.10 g of Additie RC8221 (corrosion inhibitor). The mixture was homogeneized with a homogeneizer mixer at a speed of 15 m·s$^{-1}$ during 15 minutes and heated at a temperature of 35° C. Then, 0.40 g of xanthan gum (rheology modifier) was added to the mixture. The mixture was homogenized with a homogenizing mixer at a speed of 15 m·s$^{-1}$ during 15 minutes at a temperature of 35° C. 80.01 g of deionized water was slowly added to the mixture. The mixture was left to stand for 2 h30. Then, 0.30 g of Moussee S 9092 (antifoam agent) was added. The mixture was homogenized with a homogenizing mixer at a speed of 15 m·s$^{-1}$ during 30 minutes at a temperature of 35° C. The gel-based matrix of aqueous ink obtained was cooled at room temperature (25° C.). Then, 1 mL of the obtained gel-based matrix of aqueous ink was mixed with 0.025 g of retinyl acetate (Sigma-Aldrich). The mixture was homogeneized with a homogeneizer mixer at a speed of 400 rpm during 15 minutes.

In a second step (ii), 100 μL of a solution of silver nitrate (Carl Roth) (100 mM) was introduced into the mixture at a speed of 400 rpm during 15 minutes.

After the addition of the solution of silver nitrate by continuous injection, the color of the aqueous gel ink was dark grey.

The average particle size of the silver nanoparticles present within the aqueous gel ink is of 70 nm by analysis of 2D images (microscope: JEOL ARM 200), according to the standard ISO9001:2015.

When the obtained aqueous gel ink with variable color was written on cellulosic paper, the color changed immediately from dark grey to brown through a dissemination process of the silver nanoparticles on cellulosic paper (Table 3).

Thus, the color of the ink is not the same before application on cellulosic paper and after application on cellulosic paper over time.

Furthermore, a visual assessment of the color of this aqueous gel ink on cellulosic paper was realized over time (Table 3).

TABLE 2

Comparative example 1 - Visual assessment of the color of aqueous gel ink over time.

| Time | 0 min | 2 min | 1 hour | 1 day | 1 week (7 calendar days) |
|---|---|---|---|---|---|
| Color of the aqueous gel ink before application on cellulosic paper | Translucent yellow | Translucent yellow | Translucent yellow | Translucent yellow | Translucent yellow |
| Color of the aqueous gel ink after application on cellulosic paper | Translucent yellow | Translucent yellow | Translucent yellow | Translucent yellow | Brown |

TABLE 3

Comparative example 2 - Visual assessment of the color of aqueous gel ink over time.

| Time | 0 min | 2 min | 1 hour | 1 day | 1 week (7 calendar days) |
|---|---|---|---|---|---|
| Color of the aqueous gel ink before application on cellulosic paper | Dark Grey | Dark grey | Dark grey | Dark grey | Dark grey |
| Color of the aqueous gel ink after application on cellulosic paper | Brown | Brown | Brown | Brown | Brown |

The invention claimed is:

1. A process for preparing in situ an aqueous gel ink with fixed color comprising the following steps:
   (i) preparing a gel-based matrix of aqueous ink comprising ester(s) of retinol represented by the following formula (I):

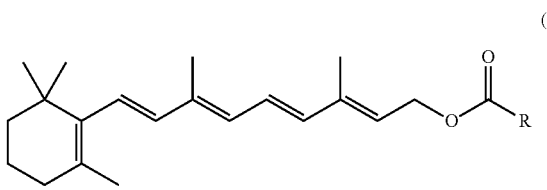

(I)

Wherein R represents a $C_1$-$C_6$ aliphatic group, said aliphatic group being optionally substituted with at least one hydroxy, halogen, amino, $C_1$-$C_3$ alkyl and/or $C_1$-$C_3$ alkoxy group, said aliphatic group being $C_1$-$C_6$ alkyl group, and
   (ii) adding a solution of gold salts ($Au^{3+}$) to the gel-based matrix of aqueous ink prepared in step (i), to obtain an aqueous gel ink with fixed color with gold nanoparticles dispersed therein.

2. The process according to claim 1, wherein the ester(s) of retinol (I) is retinyl acetate (vitamin A acetate).

3. The process according to claim 1, wherein the concentration of said ester(s) of retinol (I) in the gel-based matrix of aqueous ink of step (i) ranges from 0.10 to 0.50 mol·$L^{-1}$.

4. The process according to claim 1, wherein the concentration of gold salts ($Au^{3+}$) in the gel-based matrix of aqueous ink of step (ii) ranges from 0.004 to 0.05 mol·$L^{-1}$.

5. An aqueous gel ink with fixed color obtained according to the process of claim 1, comprising said ester of retinol (I) and gold nanoparticles.

6. The aqueous gel ink according to claim 5, wherein the amount of said ester of retinol (I) ranges from 3 to 5.5% by weight relative to the total weight of the aqueous gel ink.

7. The aqueous gel ink according to claim 5, wherein the gold nanoparticles have an average particle size ranging from 10 to 250 nm.

8. The aqueous gel ink according to claim 5, wherein the gold nanoparticles are gold nanoparticles with the shape of spheres.

9. The aqueous gel ink according to claim 5, wherein the amount of gold nanoparticles ranges from 0.05 to 3% by weight relative to the total weight of the aqueous gel ink.

10. The aqueous gel ink according to claim 5, wherein the amount of water ranges from 50 to 95% by weight relative to the total weight of the aqueous gel ink.

11. The aqueous gel ink according to claim 5, further comprising a solvent chosen in the group consisting of glycol ethers, in an amount ranging from 5 to 35% by weight relative to the total weight of the aqueous gel ink.

12. The aqueous gel ink according to claim 5, further comprising an antimicrobial agent, in an amount ranging from 0.01 to 0.5% by weight relative to the total weight of the aqueous gel ink.

13. The aqueous gel ink according to claim 5, further comprising a corrosion inhibitor, in an amount ranging from 0.05 to 1% by weight relative to the total weight of the aqueous gel ink.

14. The aqueous gel ink according to claim 5, further comprising an antifoam agent, in an amount ranging from 0.05 to 1% by weight relative to the total weight of the aqueous gel ink and/or a rheology modifier, in an amount ranging from 0.08 to 2% by weight relative to the total weight of the aqueous gel ink.

15. A writing instrument comprising:
   an axial barrel containing an aqueous gel ink with fixed color according to claim 5, and
   a pen body which delivers the aqueous gel ink stored in in the axial barrel,
wherein the writing instrument is chosen in the group consisting of gel pens, felt pens, correction fluid, and markers.

16. The writing instrument of claim 15, wherein the writing instrument is chosen in the group consisting of gel pens.

17. The aqueous gel ink according to claim 5, wherein the gold nanoparticles have an average particle size ranging from 50 to 200 nm.

18. The process of claim 1, wherein the aliphatic group is a $C_1$-$C_4$ alkyl group.

19. The process of claim 1, wherein the aliphatic group is unsubstituted.

20. The process of claim 1, wherein the aliphatic group is a methyl group.

* * * * *